United States Patent
Wu

[19]

[11] Patent Number: 6,163,262
[45] Date of Patent: Dec. 19, 2000

[54] URINE DETECTING AND SIGNALLING DEVICE FOR USE IN A DIAPER

[75] Inventor: Po-Chen Wu, Tainan, Taiwan

[73] Assignee: Ber-Lin Wu, Tainan, Taiwan

[21] Appl. No.: 09/270,203

[22] Filed: Mar. 15, 1999

[51] Int. Cl.$^7$ ................................................. G08B 21/00
[52] U.S. Cl. .................. 340/604; 340/573.1; 340/384.1; 604/361
[58] Field of Search ................................ 340/604, 573.1, 340/384.1, 603, 605; 604/361

[56] References Cited

U.S. PATENT DOCUMENTS

| | | | |
|---|---|---|---|
| 4,191,950 | 3/1980 | Levin et al. | 340/604 |
| 4,205,672 | 6/1980 | Dvorak | 340/604 |
| 5,036,859 | 8/1991 | Brown | 340/573.1 |
| 5,266,928 | 11/1993 | Johnson | 340/604 |
| 5,392,032 | 2/1995 | Kline et al. | 340/604 |
| 5,459,452 | 10/1995 | DePonte | 340/604 |
| 5,568,128 | 10/1996 | Nair | 340/604 |
| 5,760,694 | 6/1998 | Nissim et al. | 340/604 |
| 5,796,345 | 8/1998 | Leventis et al. | 340/604 |
| 5,808,554 | 9/1998 | Shuminov | 340/604 |

*Primary Examiner*—Nina Tong
*Attorney, Agent, or Firm*—Rosenberg, Klein & Lee

[57] ABSTRACT

Urine detecting and signalling device for use in a diaper includes two pieces of flat conductive foil and a control unit. The two pieces of the foil are positioned under an absorbent material of the diaper. Each of the foil has an inner end located in the diaper, and an outer end protruding from lateral side of the diaper. The control unit has two end conductors, and a circuit electrically connected to the end conductors. The control unit is detachably fitted on the diaper with the end conductors electrically connected to the outer ends of the foil. The circuit and the foil are completed by urine of the diaper flowing into the absorbent material to activate a load of the circuit to alert the attending person.

2 Claims, 11 Drawing Sheets

URINE DETECTING AND SIGNALLING DEVICE FOR USE IN A DIAPER

BACKGROUND OF THE INVENTION

Figure 12:
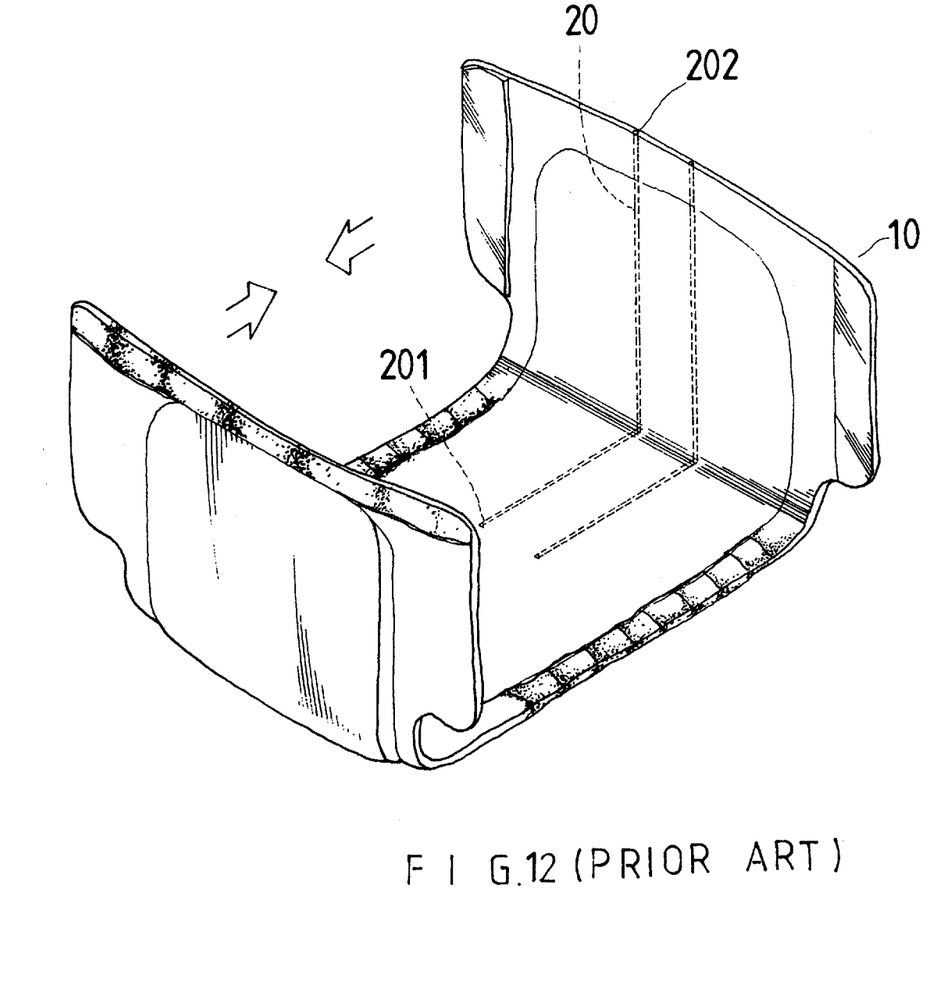
FIG. 12 is a view showing the appearance of a heretofore diaper as described in the Background.
Figure 13:
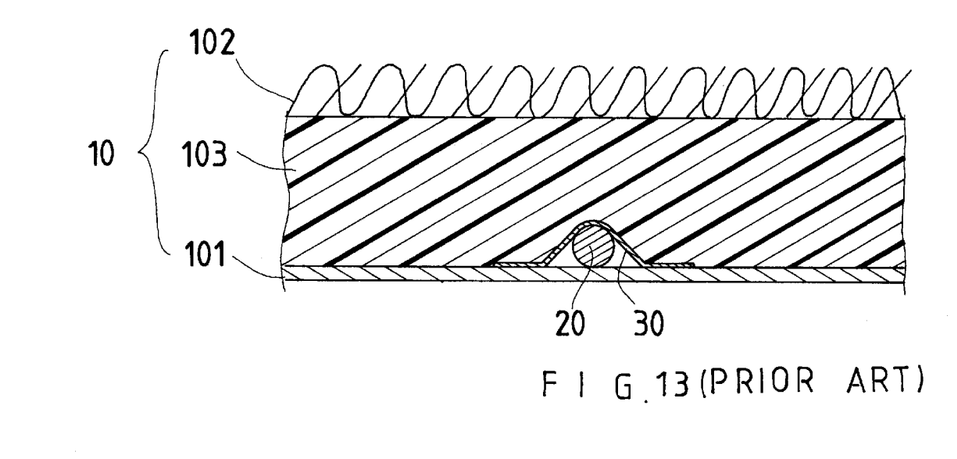
FIG. 13 is a fragmentary sectional view of the diaper of FIG. 12.

Referring to FIGS. 12 and 13, a heretofore known diaper 10 has a waterproof layer 101, an uppermost layer 102 and an absorbent material 103 between the layers 101 and 102; the waterproof 101 can be made of PE plastic; the uppermost layer 102 can be nonwoven fabrics. A urine detecting and signalling device is fitted to the diaper 10; the urine detecting and signalling device comprises two conducting wires 20 positioned between the waterproof layer 101 and the absorbent material 103; adhesive tape 30 is used to secure the wires 20 on the layer 101. As shown in FIG. 12, the two wires 20 has same length, each having an inner end 201 contacting the absorbent material 103, and an outer end 202. A control unit is detachably connected to the outer ends 202 of the wires 20 such that when the diaper 10 is in a damp condition, the circuit consisting of the wires 20 and the control unit is completed. Thus, the control unit can send out sound or light to signal to the attending person to change the diaper promptly.

However, the urine detecting and signalling device of the diaper has undesirable features as follows.

1. In assembling, the worker has to manually apply adhesive tape to secure the wires to the diaper to prevent it from moving and rolling, making the manufacturing relatively inconvenient and labor-costing.

Figure 14:
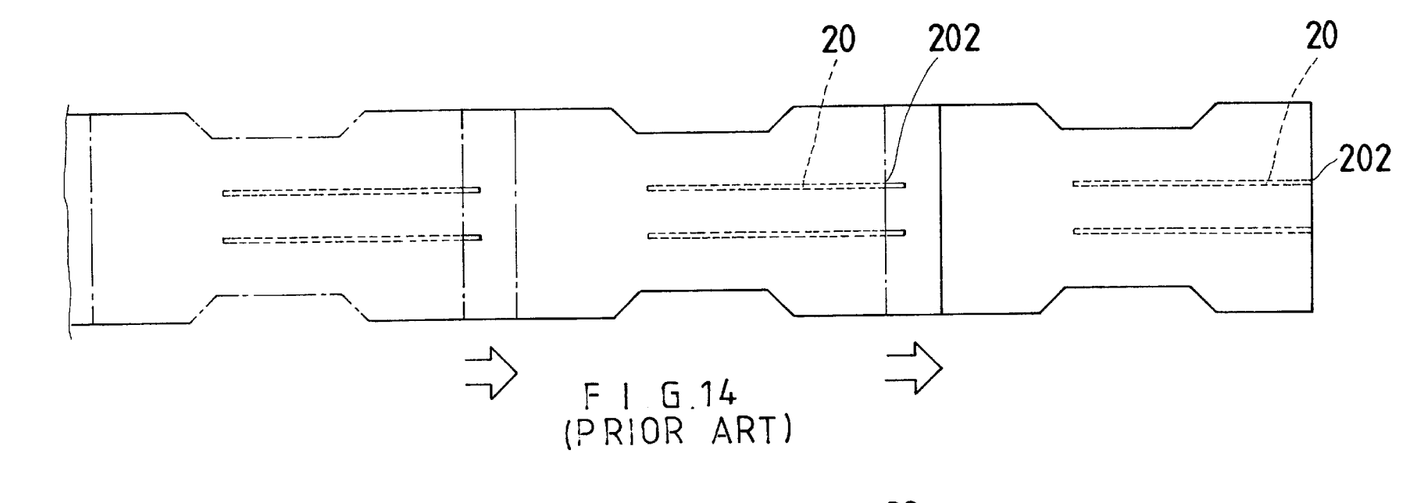
FIG. 14 is a view of semi-finished diapers as described in the Background.

2. Referring to FIG. 14, there are shown semi-finished products under common way of manufacturing, which are then cut into several finished diaper products. After the cutting, the finished diaper products each has to be opened by a worker manually from those portions contacting the outer ends of the wires in order for the control unit to be capable of connecting the wires. Therefore, the manufacturing costs relatively much time.

3. Because the workers have to separate the outer ends of the wires from the diapers, the manufacturing cannot be completely automated.

4. The wires, being usually thin and cylindrical copper wires and having relatively small contact area, have to be previously processed to be capable of firmly connecting the control unit. So, the manufacting of the diaper is inconvenient.

5. The diaper material usually contains some water (about 6%) in manufacturing of the diaper such that the material won't be too dry and fluffy for the manufacturing process. The wires are likely to rust due to the water, making the diaper dirty, losing conductivity.

6. The wearer might get hurt if the wires are not properly secured.

7. When the diaper is discared, the conducting wires attached thereto will cause environmental pollution.

SUMMARY

It is an object of the present invention to provide a urine detecting and signalling device for use in a diaper such that the attending person can be alerted to change the diaper for the wearer in time when the wearer urinates or defecates.

It is another object of the present invention to provide a urine detecting and signalling device for use in a diaper such that the diaper can be fitted with the device in manufacturing with relatively less labor and time.

It is a main object of the present invention to provide a urine detedting and signalling device for use in a diaper that would not hurt the wearer or cause environmental problem when the diaper is diacarded.

The urine detecting and signalling device includes two pieces of flat conductive foil and a control unit. The two pieces of foil are positioned under an absorbent material of the diaper and they are bent such that two outer ends extend from lateral side of diaper to be capable of electrically connecting the control unit. The control unit has two end conductors, a magnifying circuit and a load. Each of the end conductors contacts a respective one of the foil outer ends when the control unit is fitted to the diaper. The control unit associated with the foil will be completed by urine of the diaper when the wearer urinates or defecates; thus, the magnifying circuit activates the load to send out sound and light, to alert the attending person.

The control unit can be further provided with a radio transmitter therein, and works along with a signalling device having a radio receiving and translating circuit. When the wearer urinates, the radio transmitter is activated to send out a message, which is then received and translated by the circuit of the signalling device; the signalling device then send out sound and light to alert the attending person on ascertaining that the message is from the control unit.

Being flat, the foils can contact the end conductors of the control unit properly. So the manufacturers don't have to process and shape the foil as they do in manufacturing a prior art urine detecting and signalling device, which uses thin and cylindrical metal wires instead of the foil.

Being flat and soft, the foil is not likely to hurt the wear of the diaper provided with the device of the present invention.

BRIEF DESCRIPTION OF THE DRAWINGS

The present invention will be better understood by reference to the accompanying drawings, wherein.

DETAILED DESCRIPTION OF THE PREFERRED EMBODIMENT

Figure 1:
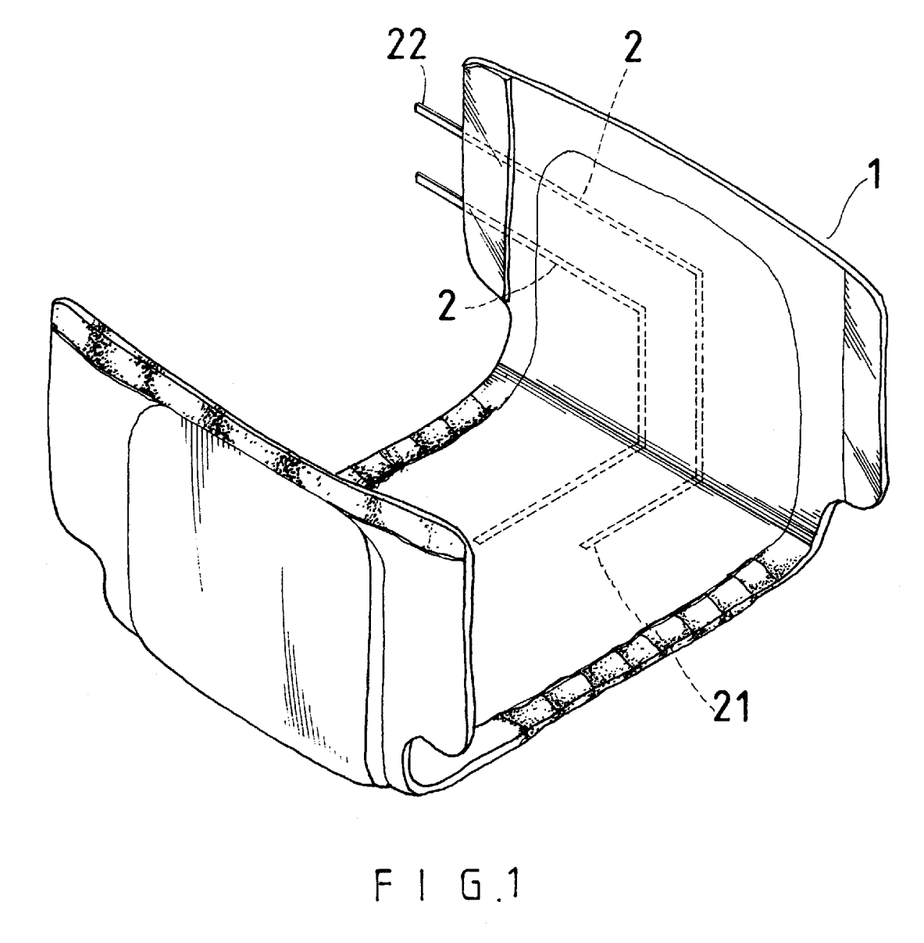
FIG. 1 is a view showing the appearance of a diaper according to the present invention.
Figure 2:
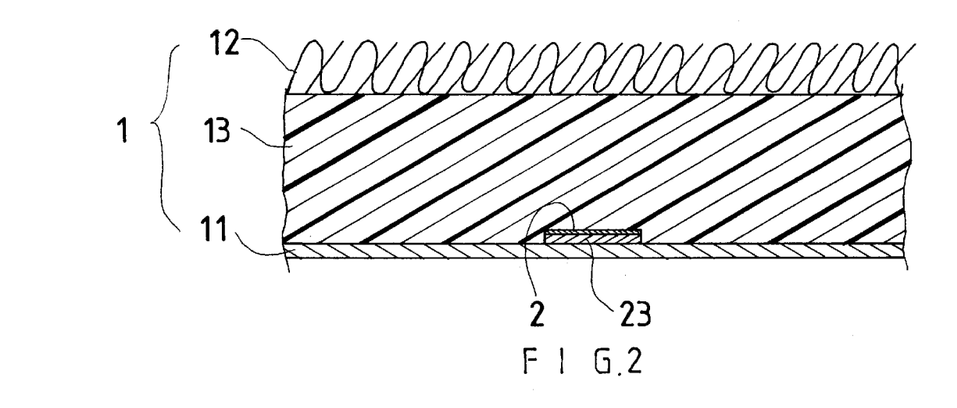
FIG. 2 is a fragmentary sectional view of the diaper of FIG. 1.

Referring to FIGS. 1 and 2, a diaper 1 of the present invention has a waterproof layer 11, an uppermost layer 12 and an absorbent material 13 between the layers 11 and 12; the waterproof layer 11 can be made of PE; the uppermost layer 12 can be nonwoven fabrics. A urine detecting and signalling device is used for the diaper.

The urine detecting and signalling device includes two pieces of conductive flat foil 2 positioned between the waterproof layer 11 and the absorbent material 13. Each of the foil 2 has an inner end 21 and an outer end 22. Both of the foil 2 have different length, as shown in FIG. 1. The inner ends 21 contact the absorbent material 13 of the diaper 1. The two pieces of the foil 2 are bent such that the outer ends 22 extend from one lateral side of the diaper 1. The foil 2 can be gold fiol, copper foil, aluminum foil, tin foil or paper with conductive glue applied thereon. The foil 2 further can be connected with a water-absorbing material at the bottom thereof, as shown in FIG. 2.

Figure 3:
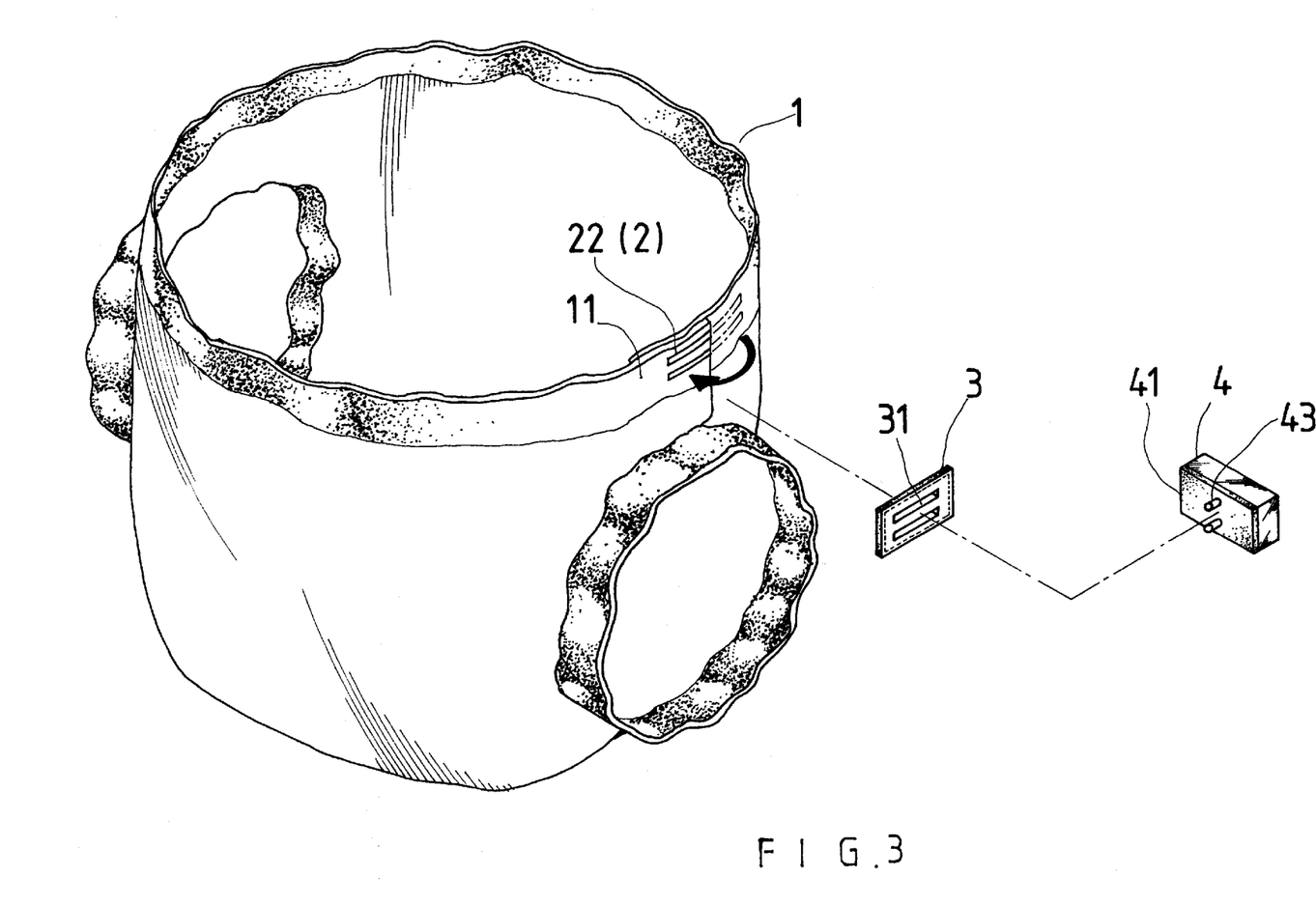
FIG. 3 is an exploded perspective view of a urine detecting and signalling device for use in a diaper of the present invention.
Figure 4:
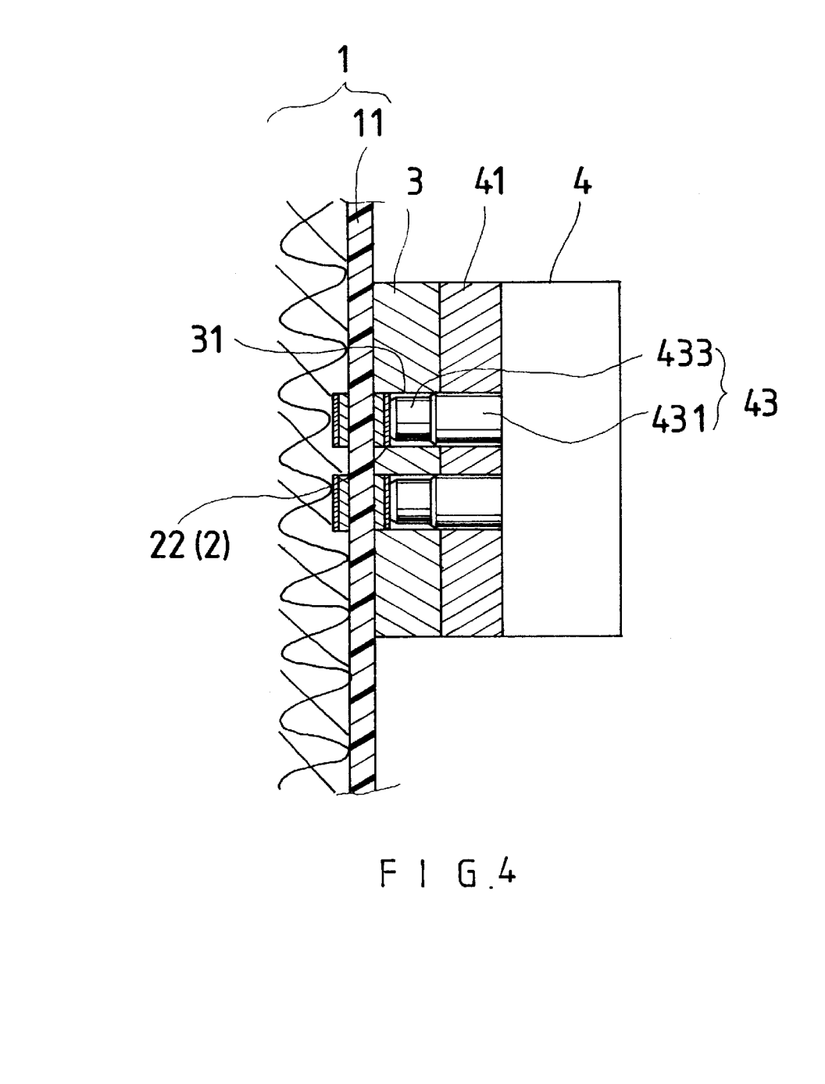
FIG. 4 is a sectional view of the urine detecting and signalling device for use in a diaper of the present invention, coupled to the diaper.

Referring to FIGS. 3 and 4, the outer ends 22 of the foil 2 are bent and secured to the outer side of the diaper 1. A Velcro 3 is sewn on the diaper 1 around the outer ends 22: the Velcro 3 has through holes 31 such that the Velcro 3 does not cover the outer ends 22 of the foil 2.

Furthermore, a contorl unit 4 is provided, which includes a housing (not numbered), a circuit 42 housed inside the housing and two end conductors 43; the end conductors 43 protrude beyond the housing and are electrically connected with the circuit 42. A Velcro 41 is fixed on the housing, adjacent to the end conductors 43 such that the control unit 4 can be detatchably fastened to the Velcro 3 of the diaper 1 for the end conductors 43 to be electrically connected to the outer ends 22 of the foil 2.

Figure 5:
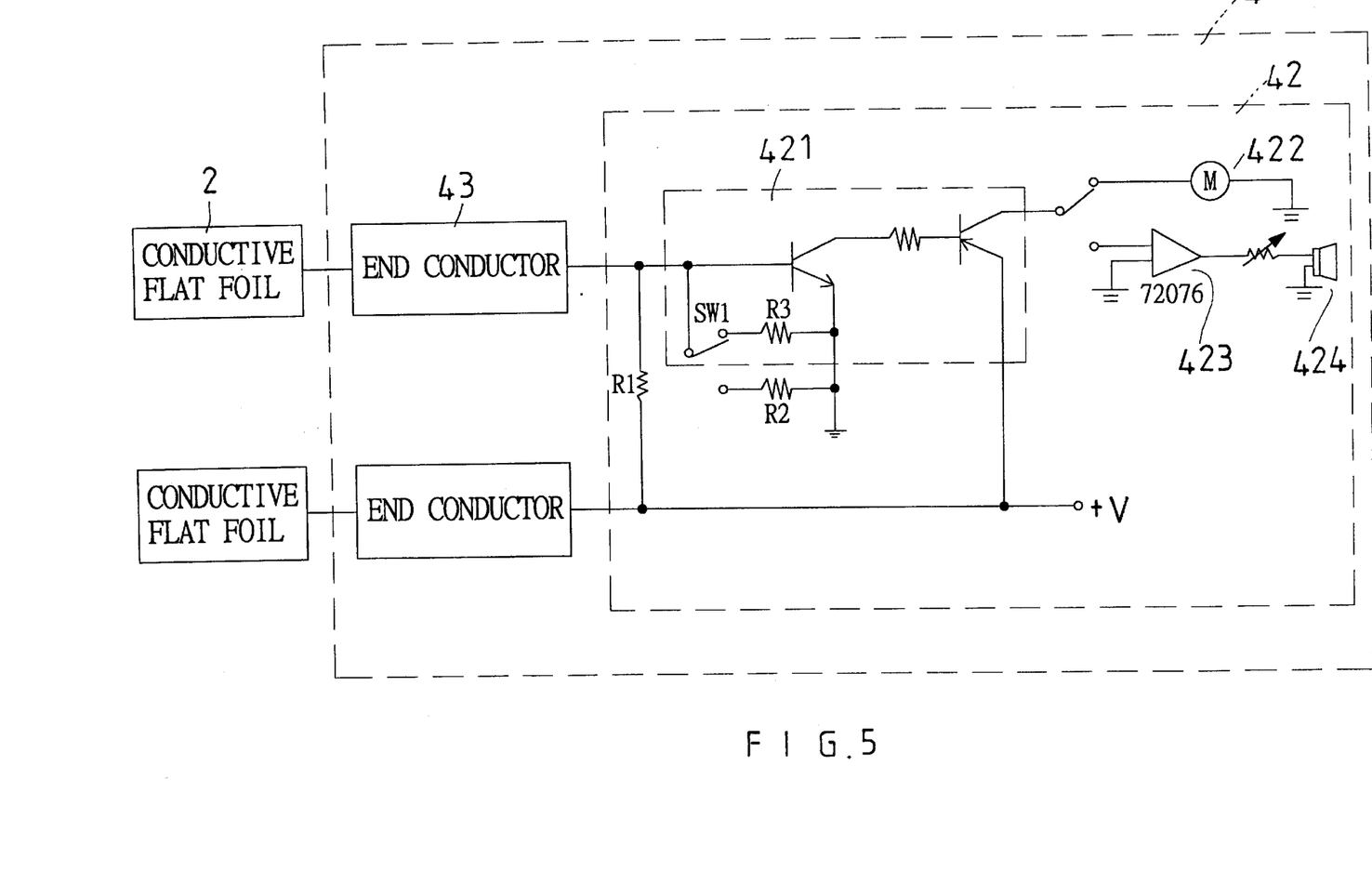
FIG. 5 is a circuit diagram of a first embodiment of a control unit of the urine detecting and signalling device for use in a diaper of the present invention.

Referring to FIG. 5, there is shown a circuit diagram of a first embodiment of the control unit 4; the control unit circuit 42 comprises a magnifying circuit 421, a vibrating motor 422, a musical IC 423 and a speaker 424. Referring again to FIGS. 1 and 2, when the wearer of the diaper urinates or defecates, and the amount of the urine is engough for the two piece of the foil 2 to be electrically connected, the circuit consisting of the foil 2 and the control unit 4 will be completed. Thus, the amplifying circuit 421 activates the vibrating motor 422 to vibrate, or the musical IC 423 associated with the speaker 424 to send out sound, or both to send out vibration as well as sound to alert the attending person to change the diaper for the wearer. In FIG. 5, resistor R1=resistor R2>>resistor R3; when SW1 is switched to R3, the above said performance can be carried out; when the SW1 is switched to R2, the user can test whether the circuit is in a good condiction.

Figure 6:
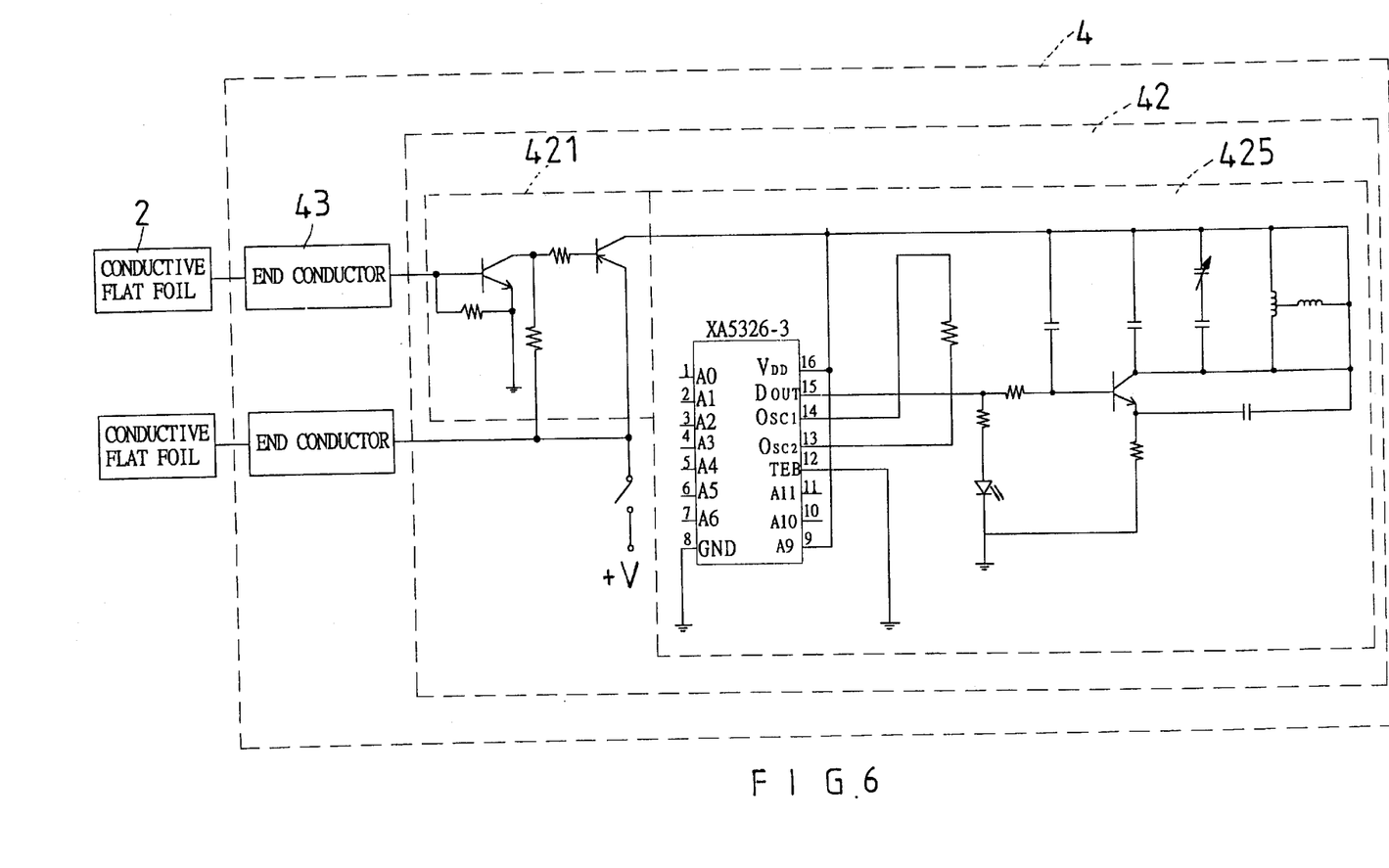
FIG. 6 is a circuit diagram of a second embodiment of a control unit of the present invention.
Figure 7:
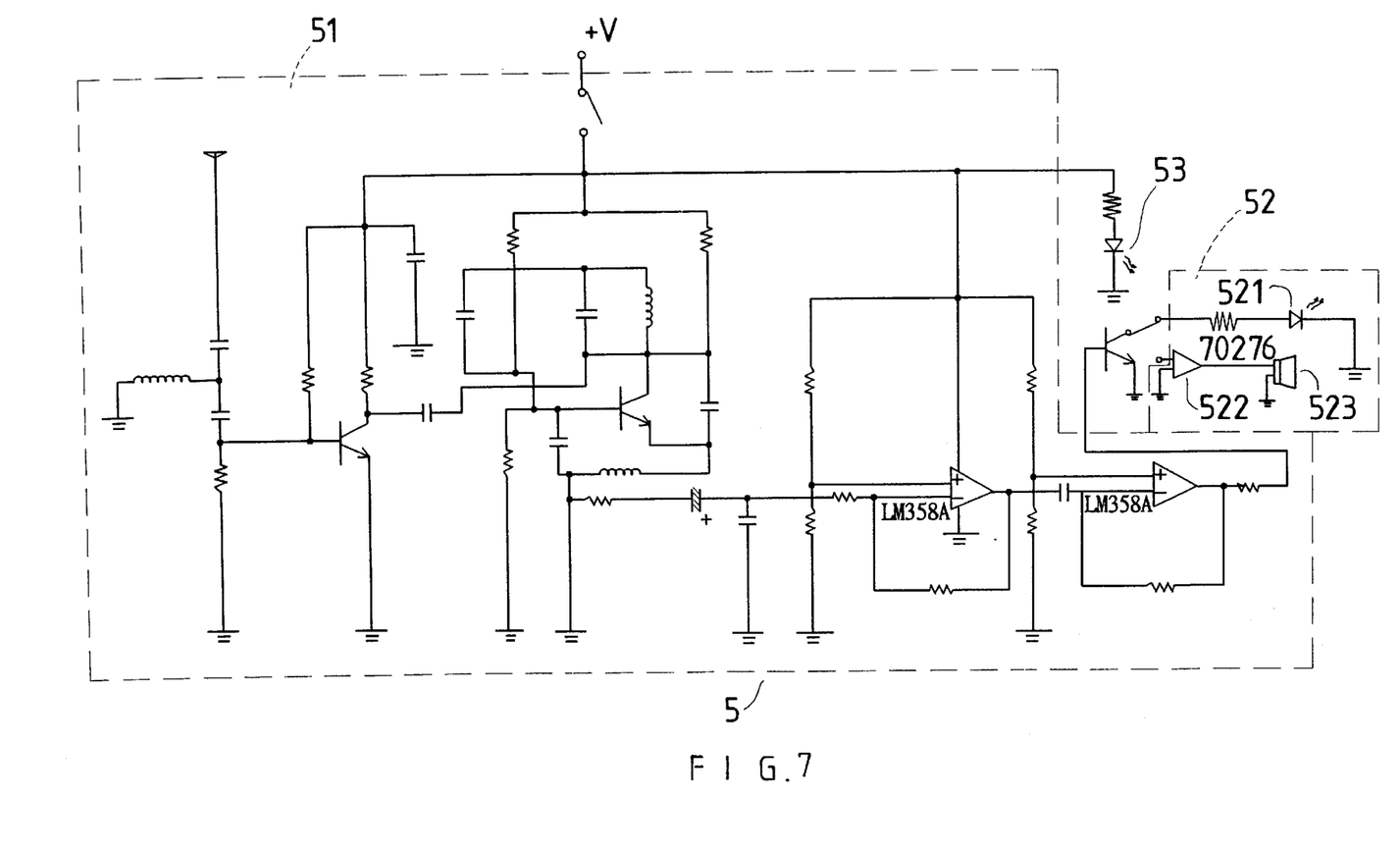
FIG. 7 is a circuit diagram of a second embodiment of a signalling device of the present invention.

Referring to FIGS. 6 and 7, there are shown a circuit diagram of a second embodiment of a control unit 4 and a circuit diagram of a first embodiment of a signalling device 5; a circuit 42 of the control unit 4 is a radio transmitter including a magnifying circuit 421 and a transmitting circuit 425; the signalling device 5 includes a receiving and translating circuit 51 and a load 52. The receiving and translating circuit 51 can receive and translate radio messages, and will activate the load 52 on determining that the message is from the control unit 4 fitted to the diaper 1. The load 52 can be an indicating light bulb 521 or a musical IC 522 associated with a speaker 523. Furthermore, a power supply indicating light 53 is connected to a power-input end of the signalling device 5. In using, the attending person carries the signalling device 5 with him/her when away from the baby or patient. When the urine in the diaper electrically connect the foil 2, the control unit 4 will be activated to send out radio message, which is then received and translated by the receiving and translating circuit 51. Thus, the signalling device 5 is activated to send out light or sound or both to alert the attending person.

Figure 8:
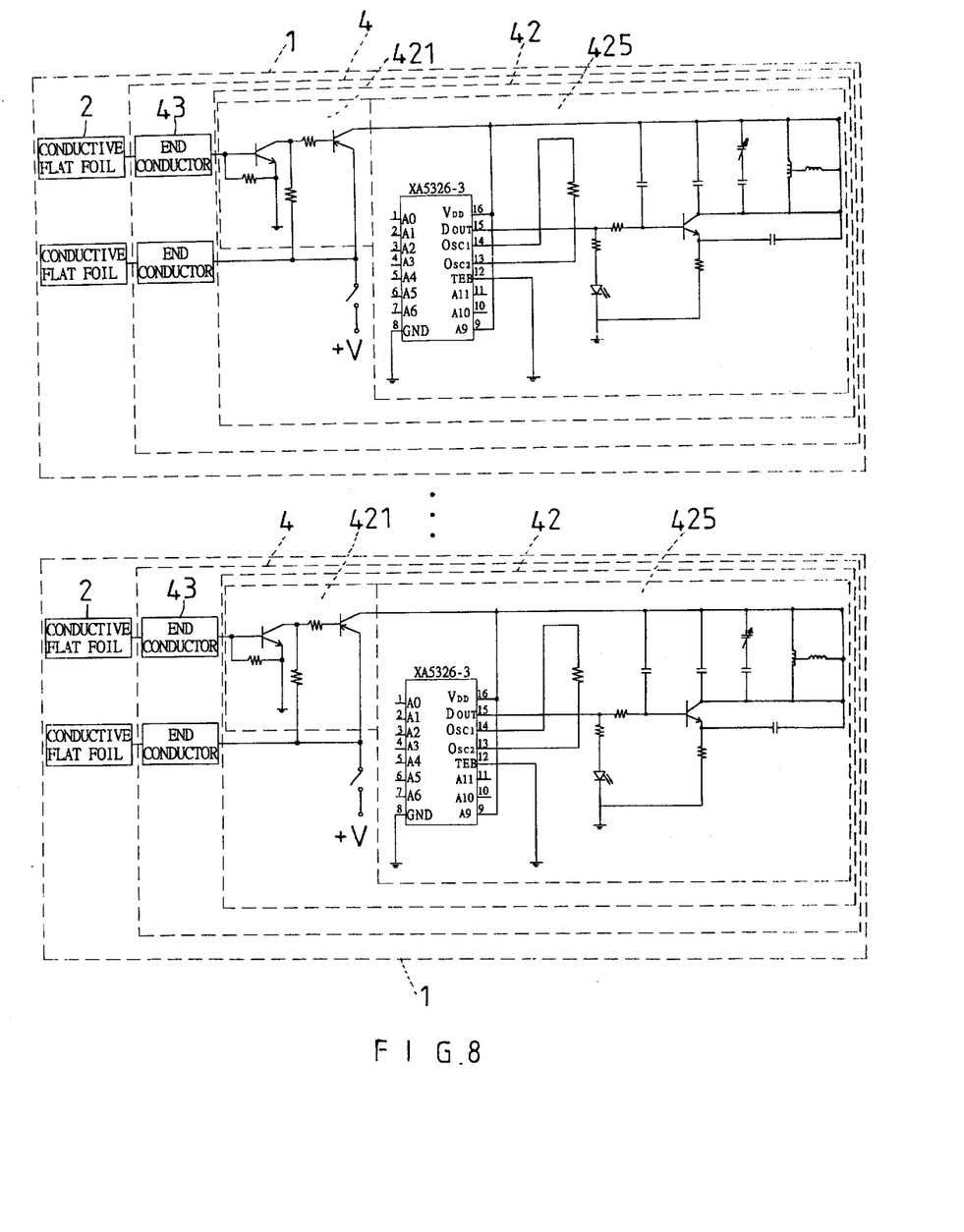
FIG. 8 is a circuit diagram of a third embodiment of a control unit of the present invention.
Figure 9:
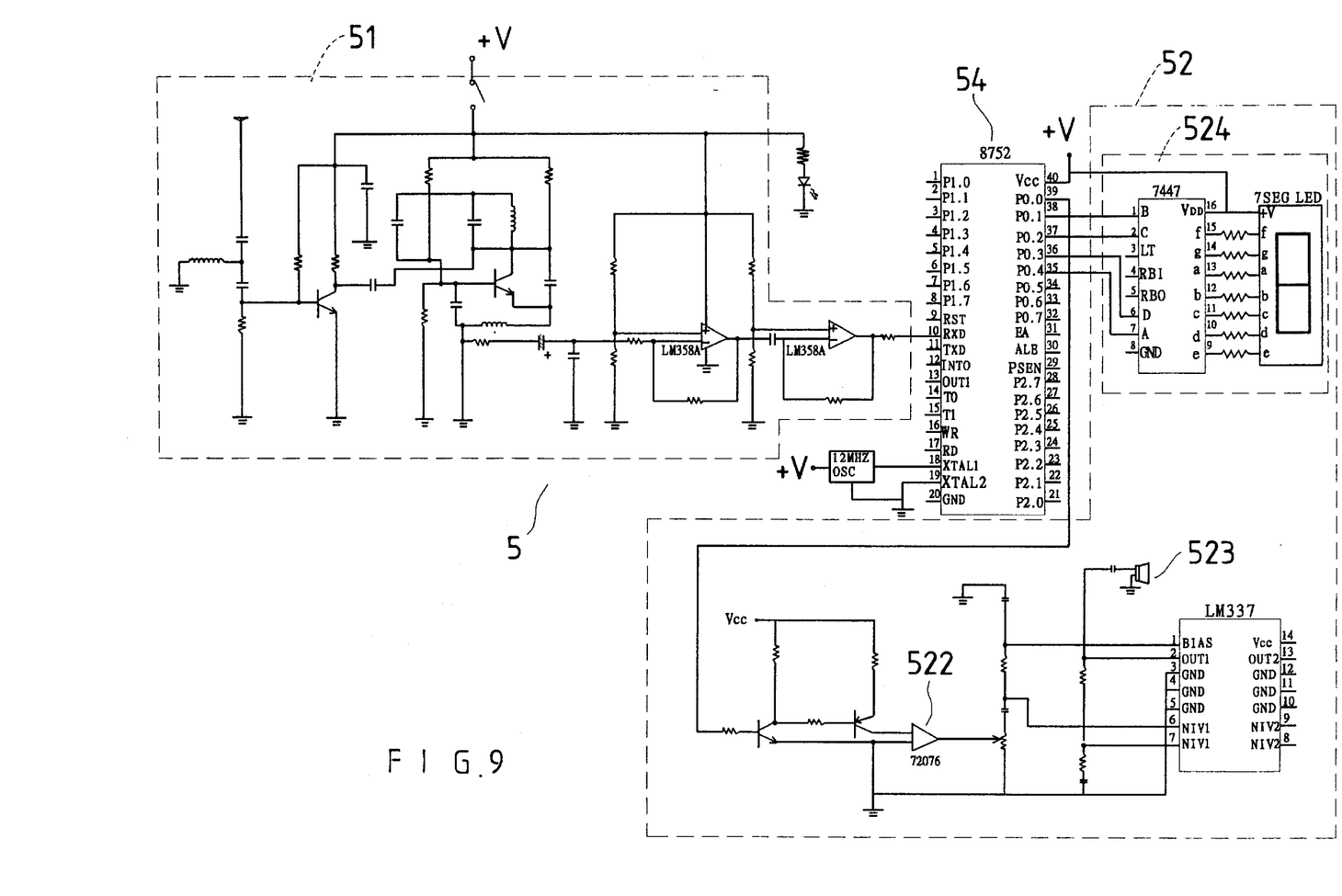
FIG. 9 is a circuit diagram of a third embodiment of a signalling device of the present invention.

Referring to FIGS. 8 and 9, there are a circuit diagram of a third embodiment of control unit 4 and a circuit diagram of a third embodiment of a signalling device 5. The signalling device 5 has a radio receiving and translating circuit 51, a CPU (central processing unit) 54 and a load 52. The load 52 is a LCD (liquid crystal display) 524 associated with a musical IC 522 and a speaker 523. There are several control units 4 each including a magnifying circuit 421 and a radio transmitting circuit 425, and fitted to a respective diaper. The diapers are worn by babies or patient in a hospital ward when one of the wearers urinates or defecates, the corresponding control unit 4 will transmit a message, which is then received by the receiving and translating circuit 51 of the signalling device 5. The message is then sent to the CPU 54 for it to determine which control unit has sent out the message. Then, the corresponding number of that control unit is shown on the LCD 524 of the signalling device 5, accompanied by sound from the musical IC 522 and the speaker 523 to alert the attending person to change the damp diaper with a clean and dry one.

Figure 10:
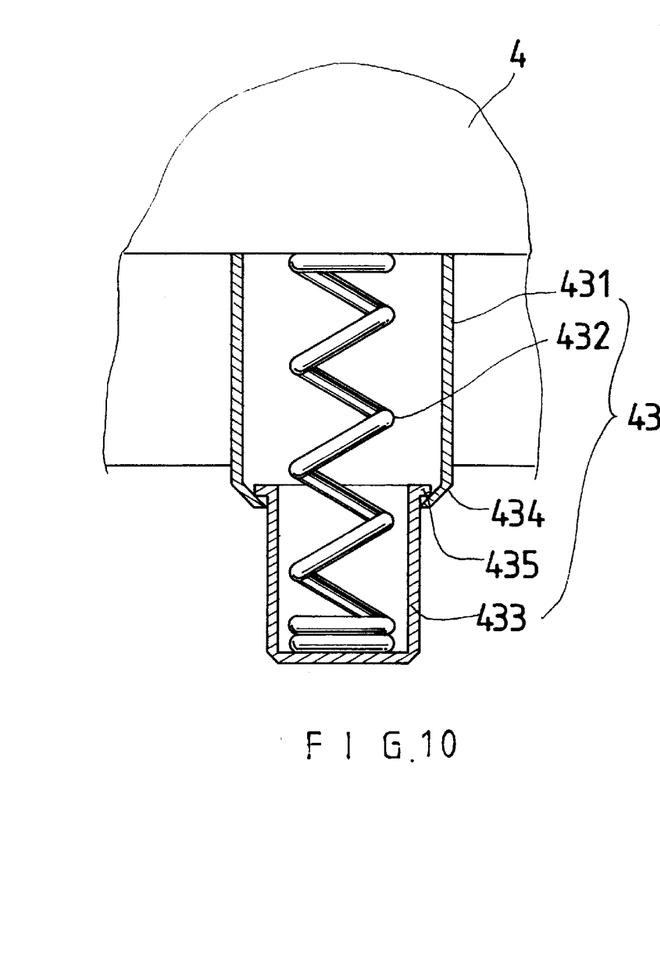
FIG. 10 is an enlarged view of an end conductor of the control unit according to the present invention.

Referring to FIGS. 4 and 10, there is an end conductor 43 of the control unit 4. The end conductor 43 comprises a socket 431, a spring 432 and a contact 433. The spring 432 is positioned inside a room formed by the socket 431 and the contact 433. The socket 431 has an engaging portion 434, which can engage an engaging portion 435 fo the contact 433 for the contact 433 to resiliently protrude out from the socket 431 under biasing force of the spring 432. Thus, when the control unit 4 is attached to the diaper, the contacts 433 of the end conductors 43 can properly contact the foil 2 on the diaper.

Referring to FIGS. 1 and 2, the two piece of the foil 2 fitted in a diaper 1 have different length, i.e. the distance between inner ends 21 of the foil 2 can be adapted for the user's demand in manufacturing. The greater the distance between the inner ends 21 of the foil 2 are the more amount of urine in the diaper is needed for activating the signalling device to alert the attending person. So, the customer can buy a diaper with the inner ends 21 of the foils spaced apart at his/her desired distance such that the signalling device will not be activated until the diaper is damp enough for changing to be necessary.

The water-absorbing paper 23 can absorb the urine inside the absorbent material 13 of the diaper to insure the contact between the urine and the foil for the control unit to function in time.

From the above description, it can be seen that the urine detecting and signalling device for use in a diaper according to the present invention has advantages as follows.

1. Being flat, the foil 2 can be easily fixed between the waterproof layer and the absorbent material of the diaper without having to use an adhesive tape.

Figure 11:
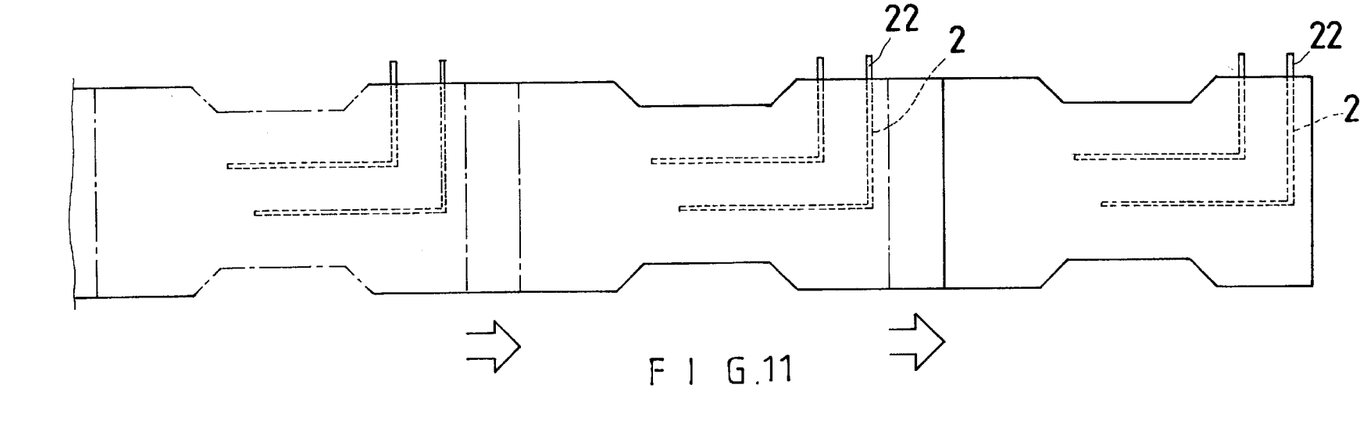
FIG. 11 is a view of semi-finished diapers of the present invention.

2. Referring to FIGS. 1 and 11, there are semi-finished diapers under common way of manufacturing, which are then cut into several separate diapers. Because the foil is bent to extend from one lateral side of the diapers, the outer ends of the foils will not be cut in cutting the semi-finished diapers, eliminating the need of the workers manually separating the outer ends from the diaper to make same stick out like the prior art.

3. The whole manufacturing process can be automated. So, time and labor cost can be reduced.

4. Being flat, the foil can be easily connected to the end conductors of the control unit without having to be first processed and shaped like the thin and cylindrical wires used in the prior art.

5. The foils inside the diaper will not rust and cause hygiene problem.

6. The foil cannot hurt the wearer.

7. When the diaper is discarded, the foil cannot cause environmental pollution.

8. The diapers are made to have the foil spaced apart at various distances, each needing a respective certain amount of urine to activate the control unit. Thus, the customers have more choices.

9. The water-absorbing paper 23 arranged on the bottom of the foil ensure the contact between the foil and the urine.

10. Being resilient, the end conductors of the control unit can contact the outer ends of the foil properly.

What is claimed is:

1. A urine detecting and signaling device for use in a diaper, comprising:

two pieces of flat conductive foil inserted between a waterproof layer and an absorbent material of the diaper, said pieces of foil each having an inner end located in the diaper, and having an outer end protruding from a lateral side of the diaper; and, a control unit having two end conductors protruding therefrom and having a circuit therein, said end conductors being electrically connected to said circuit, said end conductors being detachably connected to a respective one of said outer ends of said foil, said control unit being completed by said two pieces of said foil being electrically connected by urine of a wearer flowing into the diaper, said control unit including a radio transmitter and a magnifying circuit, and is further associated with a signaling device; said signaling device having a radio receiving and translating circuit and a load, said magnifying circuit activating said radio transmitter to send out a message to said radio receiving and translating circuit of said signaling device on said control unit responsive to urine of a wearer of said diaper flowing into said diaper, said radio receiving and translating circuit activating said load to alert a person near said signaling device on ascertaining that said message is from said control unit after said translating circuit translates said message.

2. A urine detecting and signaling device for use in a diaper, comprising:

two pieces of flat conductive foil inserted between a waterproof layer and an absorbent material of the diaper, said pieces of foil each having an inner end located in the diaper, and having an outer end protruding from a lateral side of the diaper; and, a control unit having two end conductors protruding therefrom and having a circuit therein, said end conductors being electrically connected to said circuit, said end conductors being detachably connected to a respective one of said outer ends of said foil, said control unit being completed by said two pieces of said foil being electrically connected by urine of a wearer flowing into the diaper, said control unit including a radio transmitter and a magnifying circuit, and is further associated with a signaling device;

said signaling device having a radio receiving and translating circuit, a central processing unit (CPU) and a load, said magnifying circuit activating said radio transmitter to send out a message on said control unit responsive to said foil being connected by urine in the diaper;

said radio receiving and translating circuit being capable of receiving a radio message and transmitting said message to said CPU on ascertaining that said message is from said control unit for said CPU to activate said load to send out sound and display a number corresponding to said control unit, said signaling device being capable of working with a plurality of control units each being fitted to a respective diaper and having a respective number associated therewith.

* * * * *